(12) United States Patent
Singh

(10) Patent No.: US 8,905,953 B2
(45) Date of Patent: *Dec. 9, 2014

(54) HEMODIALYSIS VEIN PREPARATION APPARATUS AND METHODS

(76) Inventor: Tej M. Singh, Los Altos Hills, CA (US)

(*) Notice: Subject to any disclaimer, the term of this patent is extended or adjusted under 35 U.S.C. 154(b) by 57 days.

This patent is subject to a terminal disclaimer.

(21) Appl. No.: 13/540,549

(22) Filed: Jul. 2, 2012

(65) Prior Publication Data

US 2012/0277692 A1   Nov. 1, 2012

Related U.S. Application Data

(63) Continuation of application No. 12/049,651, filed on Mar. 17, 2008, now Pat. No. 8,231,558.

(51) Int. Cl.
*A61H 7/00* (2006.01)

(52) U.S. Cl.
USPC ............................... 601/148; 601/152

(58) Field of Classification Search
USPC .......... 601/146, 148–152; 606/191, 192, 202, 606/203; 602/13; 128/DIG. 20
See application file for complete search history.

(56) References Cited

U.S. PATENT DOCUMENTS

| | | | |
|---|---|---|---|
| 1,629,108 A | 5/1927 | Lake | |
| 3,548,809 A | 12/1970 | Conti | |
| 5,014,681 A | 5/1991 | Neeman et al. | |
| 5,074,285 A | 12/1991 | Wright | |
| 5,186,163 A * | 2/1993 | Dye | 601/27 |
| 5,234,459 A | 8/1993 | Lee | |
| 5,383,842 A | 1/1995 | Bertini | |
| 6,010,471 A | 1/2000 | Ben-Noon | |
| 6,129,688 A | 10/2000 | Arkans | |
| 6,358,219 B1 | 3/2002 | Arkans | |
| 6,491,652 B1 | 12/2002 | Hata et al. | |
| 6,494,852 B1 | 12/2002 | Barak et al. | |
| 6,565,593 B2 | 5/2003 | Diana | |
| 6,700,031 B1 | 3/2004 | Hahn | |
| 6,852,089 B2 | 2/2005 | Kloecker et al. | |
| 6,960,159 B2 | 11/2005 | Chung et al. | |
| 7,063,676 B2 | 6/2006 | Barak et al. | |
| 7,498,477 B2 * | 3/2009 | Wada et al. | 602/53 |
| 8,231,558 B2 | 7/2012 | Singh | |
| 2005/0080366 A1 | 4/2005 | Cushman | |
| 2005/0107725 A1 | 5/2005 | Wild et al. | |

FOREIGN PATENT DOCUMENTS

| | | |
|---|---|---|
| EP | 1382306 A2 | 1/2004 |
| EP | 1382306 A3 | 6/2004 |
| WO | WO97/02783 | 1/1997 |
| WO | WO2007/024995 A2 | 3/2007 |
| WO | WO2007/024995 A3 | 3/2007 |

OTHER PUBLICATIONS

Beninson J, et al., Use of intermittent pneumatic compression in hemodialysis; Proc. Clin. Dial. Transplant Forum.1974;(4):209-13.
Leaf DA, et al.; Isometric exercise increases the size of forearm veins in patients with chronic renal failure; Am J Med Sci. 2003;325(3)115-9.

(Continued)

*Primary Examiner* — Michael A. Brown
(74) *Attorney, Agent, or Firm* — Baker Donelson

(57) ABSTRACT

Methods and apparatus for applying focused pressure to a target vessel to dilate the target vessel for hemodialysis.

50 Claims, 6 Drawing Sheets

(56) References Cited

OTHER PUBLICATIONS

Chleboun GS, et al.; Intermittent pneumatic compression effect on eccentric exercise induced swelling, stiffness, and strength loss; Arch Phys Med Rehabil.1995;76(8):744-9.

Feldman HI, et al.; Predictors of successful arteriovenous fistula maturation; Am J Kidney Dis. 2003; 42(5):1000-12.

Van Der Linden J, et al.; Forearm venous distensibility predicts successful arteriovenous fistula; Am J Kidney Dis. Jun. 2006; 47(6):1013-9.

Chin AI, et al.; Intra-access blood flow in patients with newly created upper-arm arteriovenous native fistulae for hemodialysis access; Am J. Kidney. Dis. 2004; 44(5): 850-8.

Dixon BS; Why don't fistulas mature?; Kidney Int. Oct. 2006; 70(8):1413-22. Epub Aug. 2, 2006.

Mindich BP, et al.; Enhancement of flow through arteriovenous fistula; Arch Surg. Feb. 1976;111(2):195-6.

Dai G, et al.; The effects of external compression on venous blood flow and tissue deformation in the lower leg; J Biomech Eng. Dec. 1999;121(6):557-64.

Janssen H, et al.; Hemodynamic alterations in venous blood flow produced by external pneumatic compression; J Cardiovasc Surg (Torino). 1993;34(5):441-7.

Rus R, et al.; Effect of Local Physical Training on the Forearm Arteries and Veins in Patients with End-Stage Renal Disease; Karger, Blood Purification 2003; 21:389-394.

Safe Vascular Access Through Collaborative Fistula First Initiative; Centers for Medicare & Medicaid Services, Mar. 17, 2005 Press Release.

International Search Report and Written Opinion of PCT Application No. PCT/US2009/037437 mailed May 6, 2009 (17 pgs).

Notification Concerning Transmittal of IPRP (1pg) & the International Preliminary Report on Patentability for PCT Application No. PCT/US2009/037437 mailed Sep. 30, 2010 (9 pgs).

\* cited by examiner

HEMODIALYSIS VEIN PREPARATION APPARATUS AND METHODS

CROSS-REFERENCE TO RELATED APPLICATION

This application is a continuation of U.S. patent application Ser. No. 12/049,651, entitled Hemodialysis Vein Preparation Apparatus and Methods and filed Mar. 17, 2008, the full disclosure of which is incorporated herein by reference and to which priority is claimed under 35 U.S.C. §120.

FIELD OF THE INVENTION

The application relates to end stage renal disease (ESRD) and more particularly to vessel preparation for hemodialysis.

BACKGROUND OF THE INVENTION

Many patients in the world suffer from renal failure from multiple underlying conditions including hypertension, genitourinary tract infections, and diabetes, a condition that affects about 20 million people in the United States alone.

Unfortunately, many of these renal failure patients result in progression to ESRD, which requires dialysis where the blood is filtered and when possible eventually a renal transplant. Dialysis options include temporary central catheter treatment, peritoneal dialysis and hemodialysis via fistulae or grafts placed in the arms connecting an artery and vein. The vein is accessed to allow blood to flow from the patient's vein to a dialysis machine, which has a filter that removes waste, surplus fluids, and balances electrolytes. The filtered blood is then returned to the patient's vein downstream from the arterial access site. Many patients and healthcare providers prefer hemodialysis via arms sites as the best hemodialysis option.

If the patient elects hemodialysis as a treatment option for the end stage renal disease, the following procedure is typical. The patient's arm veins are evaluated clinically and measured with duplex ultrasound to find a vein that is 3 mm or larger. A 3 mm vein is a suitable candidate for surgical connection to an artery. The patient's arm arteries are palpated for a pulse to find a target artery to which the vein is to be connected. The physician connects the target artery and vein either at the wrist or elbow depending on the best vein and its location. In this manner, the physician forms a fistula between the two vessels. In the example where the connection is made at the wrist, the fistula can be made between the radial artery and the cephalic vein at the wrist (brescia fistula). The patient is sent home with instructions to exercise his/her hand and arm during the day to increase blood flow in the artery and vein with the hope that this exercise will increase the vein size by the increased flow. One often used exercise technique involves squeezing a device such as a ball with the hope that the vein will enlarge. The patient is observed for about six to eight weeks to monitor if enlargement of the vein has occurred keeping in mind that at least a 10 mm diameter vein would provide for better quality dialysis as compared to a smaller vein diameter. If after weeks of such exercise, the vein does not enlarge or thrombose, alternative treatment options are discussed. Such alternative treatment options include another fistula placement in another location, fistula salvage by endovascular means, synthetic graft placement, or catheter placement.

Many studies have concluded that arm veins connected to arteries provide the most dependable, durable vascular access option for hemodialysis. After this procedure connecting the arm vein and artery, patients are told to wait and watch if their vein becomes large enough to be used for dialysis. It is hard to predict which veins will enlarge to the appropriate size for dialysis use. Unfortunately, many arm veins fail to dilate and enlarge enough after subjecting them to arterial flow to allow for dialysis to occur. Some patients are told that their veins are too small and others are given no justification. This results in more surgery and possible graft placement or prolonged catheter usage at higher costs to society. Each eventual procedure also has increased risks to the patient as dialysis is delayed.

In some cases where the vein is considered sufficiently large for hemodialysis, but below the 10 mm diameter target, it can be more susceptible to function loss in a relatively short period of time during the hemodialysis treatment. Fistulae last longer if the vessel used for dialysis is properly dilated to the target diameter of about 10 mm. The vein being treated undergoes significant trauma as a patient typically undergoes about three hemodialysis sessions per week. Eventually the fistula (vein) to which the artery is connected fails in that it does not stay dilated or functional. This failure can happen more quickly when the vein fails to dilate to the optimum diameter before hemodialysis. Once the vein fails, another vein and artery must be connected to provide another vein for hemodialysis. This process requires surgery and is uncomfortable and there are a limited number of veins that are suitable for dialysis.

Extensive research has shown that intermittent compression, external heat application, and topical agents like nitric oxide help dilate superficial veins. Typically, when a dialysis technician initiates dialysis treatment where a needle is place in the target vein, the technician will apply intermittent pressure on the patient's arm with their fingers to dilate the vein prior to needle placement.

There is a need to provide improved vein dilation methods and devices to sufficiently and/or effectively dilate a vein for hemodialysis or maintain vein dilation for a longer period, while a patient is undergoing hemodialysis treatment.

SUMMARY OF THE INVENTION

In one embodiment according to the invention, one or more of intermittent compression, heat, and topical vasodilating agents is applied to a section of a vein of a renal failure patient which vein requires dilation for dialysis for life maintenance. Further, either or both the heat and topical vasodilating agent can be intermittently applied as well.

In another embodiment according to the invention, a method for dilating a vein of a patient being treated for hemodialysis comprises applying an effective amount of pressure to a target vein to be accessed for hemodialysis (e.g., the cephalic, upper cephalic, or basilic vein, which are veins suitable for hemodialysis) for an effective amount of time to dilate the vein to a size suitable to provide access for hemodialysis where at least a portion of the time during which the pressure is applied is outside the clinic.

In one example, the pressure is applied intermittently to a section of the target vein with a device that is secured to the limb of the patient where the target vein resides and that includes a compression member that extends in a substantially straight direction and is adapted to extend along at least a portion of the length of a limb of the patient to effectively dilate the target vein, wherein the compression member has a width of 1-2 cm.

In another example, the pressure is applied intermittently to a section of the vein with a device, which is secured to the limb of the patient where the target vein resides and which includes a compression member that moves along a substantially straight track or path that extends along at least a portion of a limb of the patient to dilate the target vein, wherein the compression member has a width of 1-2 cm.

In another embodiment according to the invention, a method for dilating a target vein of a patient being treated for hemodialysis comprises securing a device to a limb of a patient being treated for hemodialysis, the limb being where the target vein, which is suitable for hemodialysis, resides and with the device applying an effective amount of pressure intermittently to a section of the target vein and for an effective amount of time to dilate the vein to a size suitable to provide access for hemodialysis.

In another embodiment according to the invention, a method for dilating a vein of a patient being treated for hemodialysis comprises applying intermittent pressure to a section of a target vein, which is to be accessed for hemodialysis, with a device that is secured to a limb of the patient and includes a compression member that exerts intermittent pressure on a substantially straight external surface portion of the patient's limb to which it is secured so as to dilate the target vein, which is suitable for hemodialysis and is beneath the external surface portion; wherein the compression member has a width of 1-2 cm and does not encircle the patient's limb when secured thereto.

In another embodiment according to the invention, vessel dilation apparatus for dilating a target vein of a patient being treated for hemodialysis comprises a support adapted to be secured to a limb of the patient; a compression member that is coupled to the support, the compression member configured to apply pressure along a substantially straight path extending along at least a portion of the length of a limb of the patient without encircling the limb when the support is secured to the limb of the patient to dilate the target vein, wherein the compression member has a width of 1-2 cm. The compression member may comprise at least one inflatable cell where optional first and second expandable members, each extending along the at least one inflatable cell (or all of the inflatable cells if the compression member has more than one inflatable cell) can be provided. In another alternative, the compression member may comprise an element that is movably mounted in the support member to move along a substantially straight path where optional first and second expandable members, each extending adjacent to the substantially straight path, which in this variation extends between the first and second expandable members.

The above is a brief description of some deficiencies in the prior art and advantages of the present invention. Other features, advantages, and embodiments of the invention will be apparent to those skilled in the art from the following description and accompanying drawings, wherein, for purposes of illustration only, specific forms of the invention are set forth in detail.

BRIEF DESCRIPTION OF THE DRAWINGS

FIG. 9C1 illustrates a variation of the embodiment of FIG. 9C.

DETAILED DESCRIPTION OF THE INVENTION

The following description will be made with reference to the drawings where when referring to the various figures, it should be understood that like numerals or characters indicate like elements. Further, before the present invention is described, it is to be understood that this invention is not intended to be limited to particular embodiments or examples described, as such may, of course, vary.

According to one embodiment of the invention, focused intermittent pressure is applied to a target vein that is to be used for hemodialysis. The pressure is applied along a narrow band of a patient's limb. The pressure can be applied along a narrow band of a patient's limb in a manner in which the pressure is focused on the target vein to dilate the target vein. To assist with applying pressure over a long period of time, any of the illustrated apparatus described herein can be secured to the patient's limb. The illustrated apparatus generally include a compression member, which can be a single inflatable cell or expandable member, multiple inflatable cells or expandable members, or a member that is tracked or rolled over a narrow band of the patient's limb. One example of such a tracked or rolled member is a roller member that is rotatably mounted to the support feature of the device that has been secured to the patient's limb. The compression member, which can be constructed to extend in a direction or move in a direction, extends or moves in a substantially straight direction along an axial direction of the patient's limb or along a length of the patient's limb without encircling the patient's limb and exerts pressure on a narrow, substantially straight external surface portion of the patient's limb so as to dilate the target vein (e.g., the cephalic vein) thereunder according to one configuration of the invention.

The illustrated inflation apparatus described herein are portable and allow the patient to be ambulatory during treatment. Accordingly, the treatment can be carried out completely outside the hospital or hemodialysis clinic or it can be carried out both outside and inside these facilities. As will be apparent from the following description, the patient might wear the apparatus in the hospital to maintain vein dilation up to the time of when the surgeon creates the fistula or in the clinic to maintain vein dilation up to the time of hemodialysis.

Figure 1:
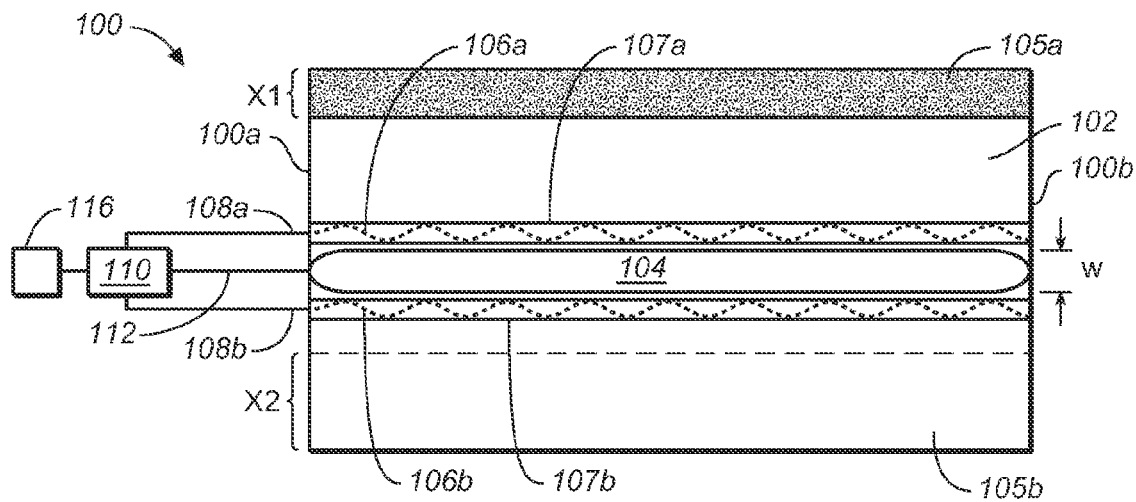
FIG. 1 is a top view of one embodiment of vein dilation apparatus according to the invention.
Figure 2:
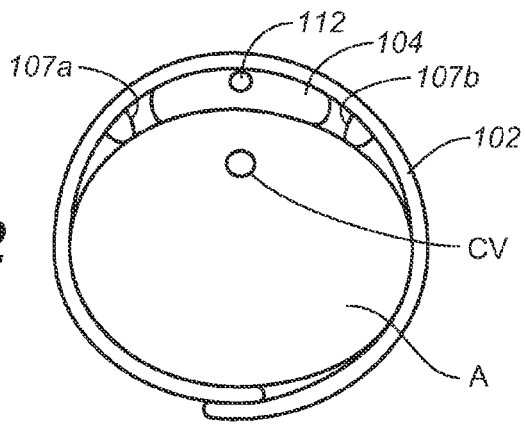
FIG. 2 is an end view of the vein dilation apparatus of FIG. 1 wrapped around a patient's arm.

Referring to FIGS. 1 and 2, one embodiment according to the invention is diagrammatically shown and generally designated with reference numeral 100. Apparatus or device 100 comprises a flexible sheet 102 and compression member 104. Flexible sheet 102 can be fabric or any other suitable material and is adapted to be placed around an arm or leg of a patient to form a sleeve. Compression member 104 in one embodiment comprises an expandable or inflatable member such as a balloon secured to flexible sheet 102. Expandable compression member 104 can be made from any suitable resilient sheet material that will sustain inflation of a fluid medium such as air and in one example can be made from nylon. In another embodiment, compression member 104 can be integrally formed with flexible sheet 102.

In the embodiment shown in FIGS. 1 and 2, compression member 104 is arranged on and secured to the inner surface of the sleeve to provide focused pressure to a target vein to be enlarged. FIG. 2 illustrates one example where apparatus 100 is wrapped around arm "A" with compression member 104 aligned over cephalic vein "CV" to provide focused pressure to the cephalic vein. Typically, element 104 will have a width "W" from 1 cm to and including 2 cm and more typically a width of 10.5 cm. This provides a low profile device suitable for long periods of use where the patient can wear the device, while maintaining normal activity. The relatively narrow width also focuses the pressure on the target zone or vein as compared to a wider inflation member or cylindrical inflation member.

Apparatus 100 has a proximal end 100a, which, for example, can be placed near the patient's elbow, and a distal end 100b, which then would be placed near the patient's wrist when the device is placed on a patient's forearm. In the illustrative embodiment, sheet 102 includes hook and loop fasteners, which can be Velcro® brand hook and loop fasteners. A band 105a of hook fasteners is provided along one side margin of sheet 102 and a band of loops along an opposite side margin 105b on the reverse side of sheet 102 (and thus hidden from view) to enable one to secure the side margins together when the sheet is wrapped to form a sleeve around a patient's limb during use. Although one hook and loop fastener configuration is shown, other configurations can be used as well as other securing mechanisms to secure portions of the sheet together when the sheet is wrapped around a patient's limb and provide the desired fit with the patient's limb for the compression member to transmit the desired pressure to the patient.

An inlet or opening is formed in compression member 104 to fluidly couple compression member 104 to a pressure source that delivers pressurized fluid such as air. The pressure source can be a compressor or pump (e.g., an air pump), which can be configured as a portable device as is known in the art. In one example, it can be a miniature device, which can be secured to the dilation apparatus or the patient with any suitable means such as a strap having hook and loop fastening portions as described above. The control unit or both the control unit and power source (described below) also can be configured to be secured to the dilation apparatus and/or the patient's limb to be carried thereby. Further, the pressure source and the control unit, which can house the pressure source, can be releasably coupled to portable apparatus 100 and the power source releasably coupled to the pressure source and/or control unit. In the embodiment illustrated in FIGS. 1 and 2, tube 112, diagrammatically represented with a line, provides a conduit between the inlet port or opening in compression member 104 and the pressure source, which is housed in control unit 110. Control unit 110 is coupled to power source 116, which can be a rechargeable battery or other suitable means for providing power to control unit 110. Control unit 110 controls activation of the pressure source, which can be preset to deliver the desired pressure. Alternatively, control unit 110 can control activation of the pressure source and pressure output from the pressure source (e.g., pump speed) to control delivery of pressurized fluid to compression member 104 at the desired pressure. In another alternative, control unit 110 can control activation of the pressure source and one or more fluid control devices such as valves, which can be operatively coupled to conduit 112 and control unit 110 in a manner such that control unit 110 controls delivery of pressurized fluid to compression member 104. In one example, control unit 110 has a timing circuit and controls pressure delivery from the pressure source to provide intermittent pressure or to intermittently provide a target or peak pressure in inflatable compression member 104 based on the timing circuit. For example, the timing circuit can provide a pressurization cycle where the pressure source delivers the desired pressure (e.g., sufficient pressure to inflate compression member 104 so that it applies sufficient pressure to the patient's limb to occlude blood flow in the target vessel) for a predetermined period of time followed by a predetermined period of time of no pressure delivery or deflation, and this repeated for a preset period of time. The desired pressure applied to the patient's limb can be from about 6 mmHg to about 25 mmHg. Depending on the patient, more pressure can be used if required for vessel occlusion or less pressure may be suitable. An on-off switch can be provided and operatively coupled to control unit 110 (e.g., between the control unit and the power source) to provide a means to start or stop the treatment period. In one arrangement, a solenoid valve can be placed in conduit 112 and operatively coupled to control unit 110 so that control unit 110 controls flow of pressurized fluid to compression member 104 through the solenoid valve based on the timing circuit.

In one variation, sheet 102 can be provided with heating elements 106a and 106b that are positioned along the side of the compression member 104 to enhance dilation of the target vessel. However, it should be understood that these heating elements are optional and are not required. Each heating element can be a conventional heating wire that is sandwiched between sheet 102 and another piece or layer of fabric 107a and 107b, respectively. Leads 108a,b connect heating elements to control unit 110, which delivers the desired power to heating elements 106a,b. Although one heating element configuration is shown, any conventional heating element arrangement can be used. In one variation, temperature sensors can be secured to the heating regions where the heating elements reside in any manner known to one of skill in the art and coupled to control unit 110, which can control power output to the heating elements in response to the sensed temperature to maintain the temperature in these regions to be from about 98 to about 150° F.

In another variation a topical dilating agent (e.g., nitric oxide) is applied to the patient's skin in the region of the target vein before securing the dilation device to the patient with the compression member aligned with the target vessel. The topical agent also can enhance vessel dilation.

Figure 3:
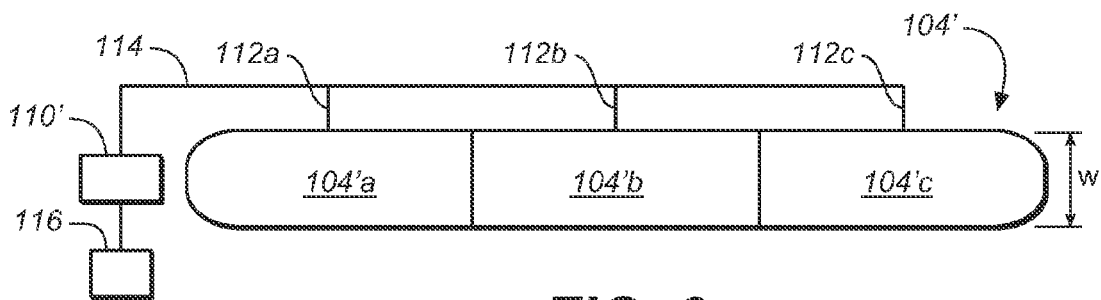
FIG. 3 illustrates a variation of the apparatus of FIG. 1 and diagrammatically illustrates a control circuit for controlling inflatable member inflation.

Referring to FIG. 3, another compression member for use in apparatus 100 is shown. The dilation apparatus embodiment incorporating the compression member of FIG. 3 into the apparatus of FIG. 1 is the same as the embodiment of FIG. 1, with the exception that the compression member configuration differs and the control unit and pressurization conduits modified to accommodate the multi-cell compression member of FIG. 3. In this embodiment, the compression member, which is designated with reference numeral 104', includes a plurality of separate expandable or inflatable compartments or cells (e.g., compartments or cells 104'a, 104'b, and 104'c) that can be inflated and/or deflated according to a desired sequence. For example, they can be inflated serially in a manner that provides a moving compression wave in one direction (e.g., from cell 104'a to cell 104'c or from cell 104'c to cell 104'a) and that cycle repeated for a desired period of time. Compression cells 104'a, 104'b, and 104'c are fluidly coupled to manifold 114 through conduits 112a, 112b, 112c and manifold 114 is fluidly coupled to a pressure source in control unit 110' so that control unit 110' can selectively provide pressure (e.g., pneumatic pressure) to the compression cells according to a predetermined sequence. Any suitable known pressure source such as described above and control mechanism can be used to control fluid delivery to cells 104'a, 104'b, and 104'c and sequentially pressurize the cells according to the desired sequence. Control unit 110' can include a timing circuit to control when fluid under pressure is to be delivered to the cells as described above and to control the cell inflation sequence. Further, a plurality of solenoid valves, which are well known mechanisms for controlling fluid flow, can be operatively coupled to the control unit 110' and conduits 112a,b,c, and control unit 110' provided with a timing circuit so that control unit 110' can control independent pressurization and venting of each compression member cell. Various solenoid valve configurations, which can be used, are disclosed, for example, in U.S. Pat. No. 6,852,089 to Kloecker et al and entitled Compression Garment for Selective Application for Treatment of Lymphedema and Related Illnesses Manifested at Various Locations of the Body, the disclosure of which is incorporated herein by reference. Cell 104'a can be inflated while the other cells are deflated, then cell 104'b inflated while cell 104'a deflated, and then cell 104'c inflated while cell 104'6 deflated and that cycle repeated for the treatment period. Alternatively, a single cycle can correspond to successively inflating the cells in one direction until they are all inflated and then deflating all of the cells as described in U.S. Pat. No. 6,010,471 to Ben-Noon and entitled Body Treatment Apparatus, the disclosure of which is hereby incorporated herein by reference.

It also should be understood that although three expandable compartments or cells are shown in the illustrative embodiment, more or fewer compartments or cells can be used.

When pressurized, the pressure in any one of the expandable elements or cells described above provides the desired pressure on the patient's limb as described above (e.g., sufficient pressure is applied to the patient's limb to occlude blood flow in the target vessel) beneath the respective cell. The control unit can be set to provide this pressure.

Compression member 104' has the same width as compression member 104. As described above, a relatively narrow width focuses the pressure of the compression member on the target vein as compared to a wider inflation member or a cylindrical inflation member.

Figure 4:
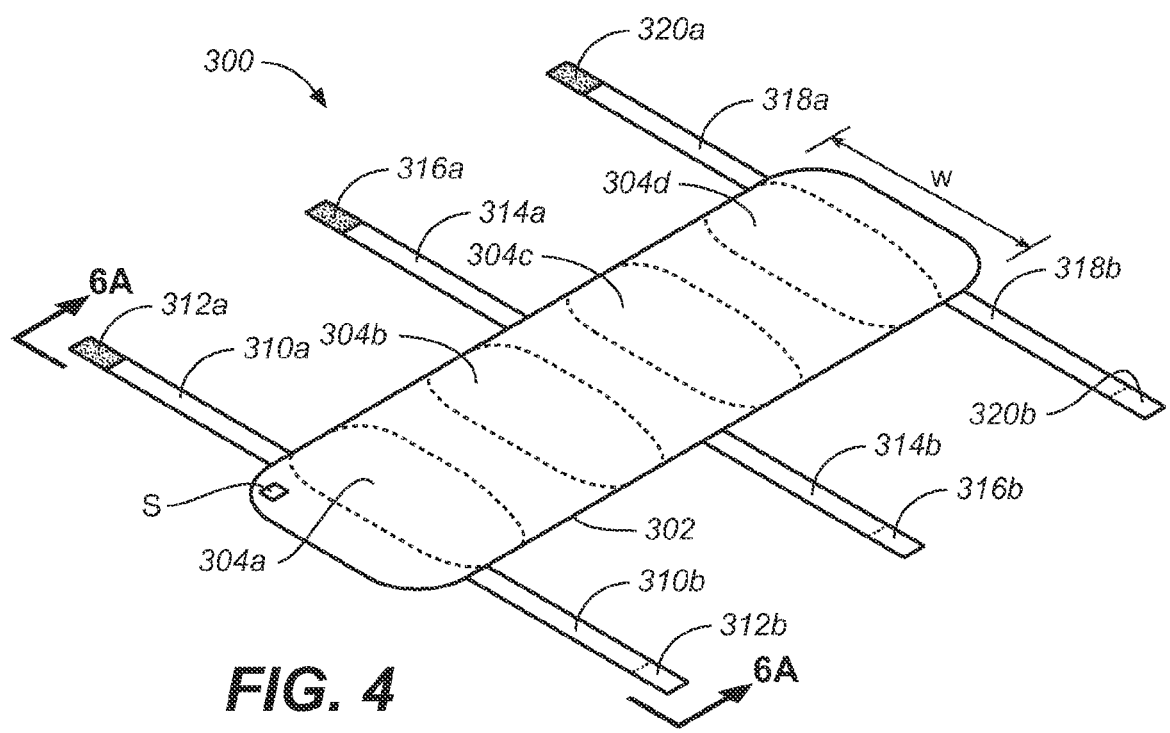
FIG. 4 is a perspective view of another embodiment of vein dilation apparatus according to the invention.
Figure 5:
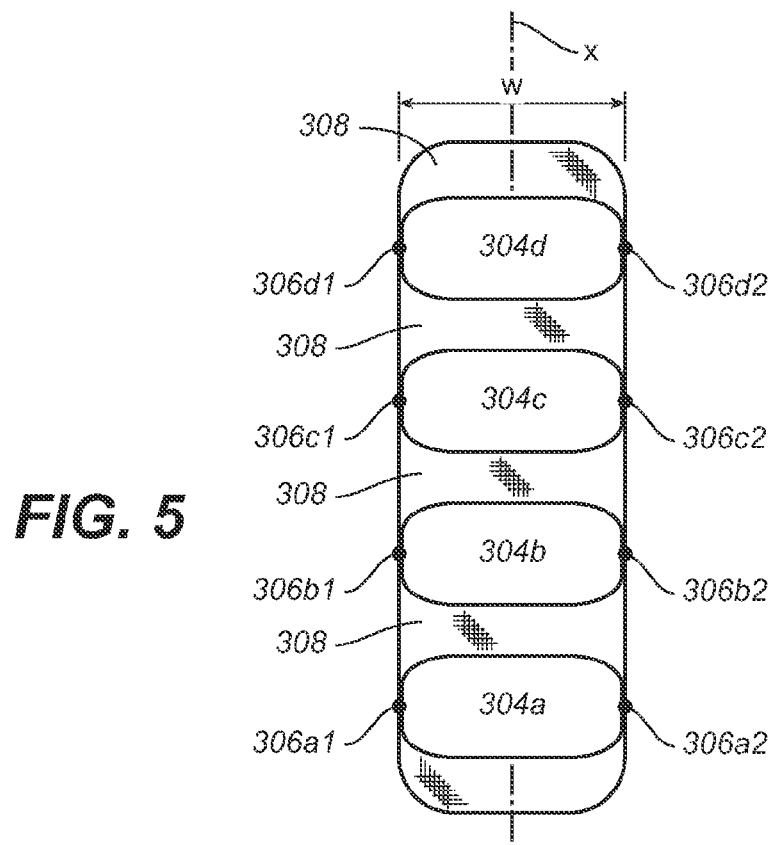
FIG. 5 is a bottom plan view of the vein dilation apparatus of FIG. 4.

Referring to FIGS. 4-6, another embodiment is shown and generally designated with reference numeral 300. Dilation apparatus or device 300 includes housing or casing 302 and a compression member comprising a plurality of separate, longitudinally spaced inflatable balloons or cells housed in casing 302 and secured thereto. Although four inflatable cells 304a,b,c,d are shown, more or fewer inflatable cells can be used. The casing typically will be a little longer (e.g., about 2 cm longer) than the treatment length of the apparatus, which corresponds to the distance between far ends of compression members 304a and 304d, and the components therein typically are selected to minimize the height of the device. As shown in the illustrative embodiment, casing 302 can have a straight configuration along its length and the expandable members arranged along a straight line with their outer edges in mating relation and aligned with the inner side walls of casing 302 as shown. The width of casing 302 is slightly larger than width "W" of the inflatable cells, which is the same as the width of compression members 104 and 104'. Typically, casing 302, which is diagrammatically shown in FIGS. 4 and 5, will have a width of 3-6 cm. This configuration provides a construction that can be readily aligned with a target vein to focus pressure on the target zone or vein as compared to larger devices including devices comprising cylindrical inflation members. The low profile of the casing enhances the ability for one to wear the device for longer periods of time and/or to wear the device while being active. In one embodiment, casing 302 is a hard, rigid material, which can be plastic. The rigid aspect provides various advantages including a mechanism to protect the treated area, which may have become bruised during hemodialysis.

Figure 6A:
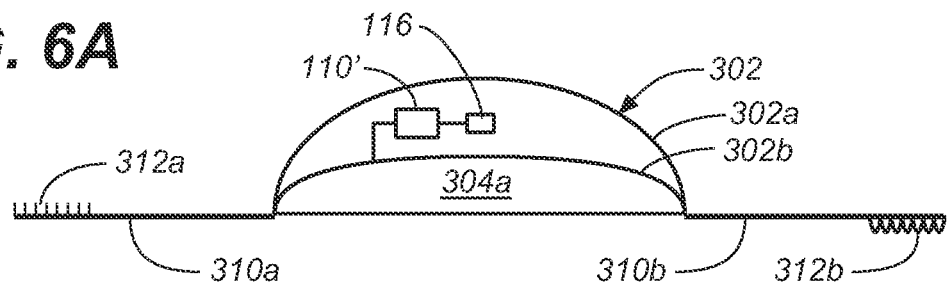
FIG. 6A is an end view of the apparatus of FIG. 5 with one of its inflatable members shown in an uninflated state.
Figure 6B:
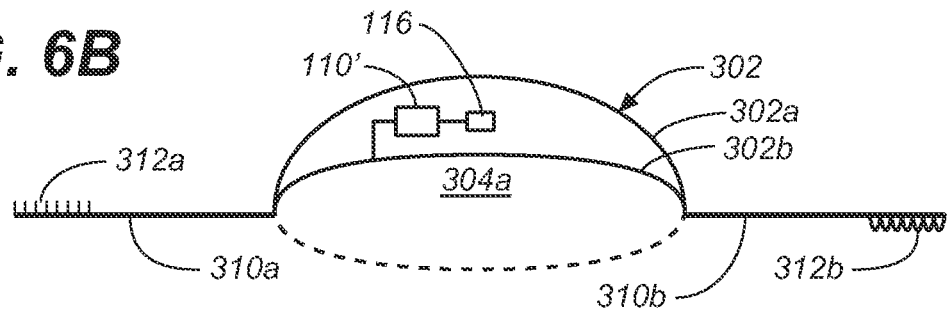
FIG. 6B is an end view of the apparatus of FIG. 5 with one of its inflatable members shown in an inflated state.

Straps 310a,b, 314a,b, and 318a,b extend from casing 302 and include cooperating pairs of fastening mechanisms 312a and 312b, 316a and 316b, and 320a and 320b, which can be Velcro® brand hook and loop fasteners or any other suitable fastening mechanism. FIGS. 6A and 6B show a side view of the engaging portions 312a and 312b.

Referring to FIG. 5, which shows a bottom plan view of dilation apparatus 300, the inflatable cells can be symmetrically aligned along the longitudinal axis "X" of casing 302. A waterproof layer of material 308, such as latex, also can be provided between the inflatable cells. Alternatively, the layer of waterproof material can be provided over the entire bottom surface of casing 302 (including the inflatable cells) so as to provide a waterproof surface over the entire area that contacts the patient's limb. In one variation, heating elements can be provided as described above in connection with the embodiment of FIG. 1. In another variation, the heating elements can comprises a plurality of heating node pairs 306a1 and 306a2, 306b1 and 306b2, 306c1 and 306c2, and 306d1 and 306d2, which are positioned on opposite sides of each inflatable cell and coupled to a power source through a control unit such as control unit 110' and power source 116.

Referring to FIGS. 6A and 6B, casing 302 can comprise an outer wall 302a and inner wall 302b to which the inflatable cells or balloons are secured or mounted. The space between walls 302a and 302b provides a chamber in which power source 116, control unit 110' (including a miniature pneumatic pump), and conduits connecting the inflatable cells to the pneumatic pump in a manner similar to that described in connection with the embodiment illustrated in FIG. 3 can be placed to control the inflation sequence of inflatable cells 304a,b,c,d as described above. Power source 116 can be any suitable power source as described above and can be a battery housed in casing 302 as shown. The battery can be a rechargeable or non-rechargeable DC battery and the pump a DC pump. An on-off switch "S" (FIG. 4) can be provided on the outer surface of apparatus 300 to disconnect the power source from the control unit and pressure source (e.g., the pump) or otherwise start or stop the apparatus. Alternatively, either or both the control unit and power source can be mounted on the outer surface of casing 302 or remote therefrom. Solenoid valves can be operatively coupled to the cells and control unit to control fluid flow as described above. FIG. 6A shows cell 304a in an uninflated or unexpanded state and FIG. 6B shows cell 304a in an inflated or expanded state.

Figure 7:
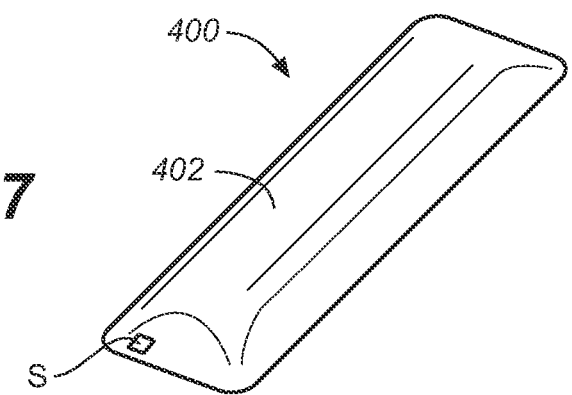
FIG. 7 illustrates another embodiment of vein dilation apparatus according to the invention.
Figure 8:
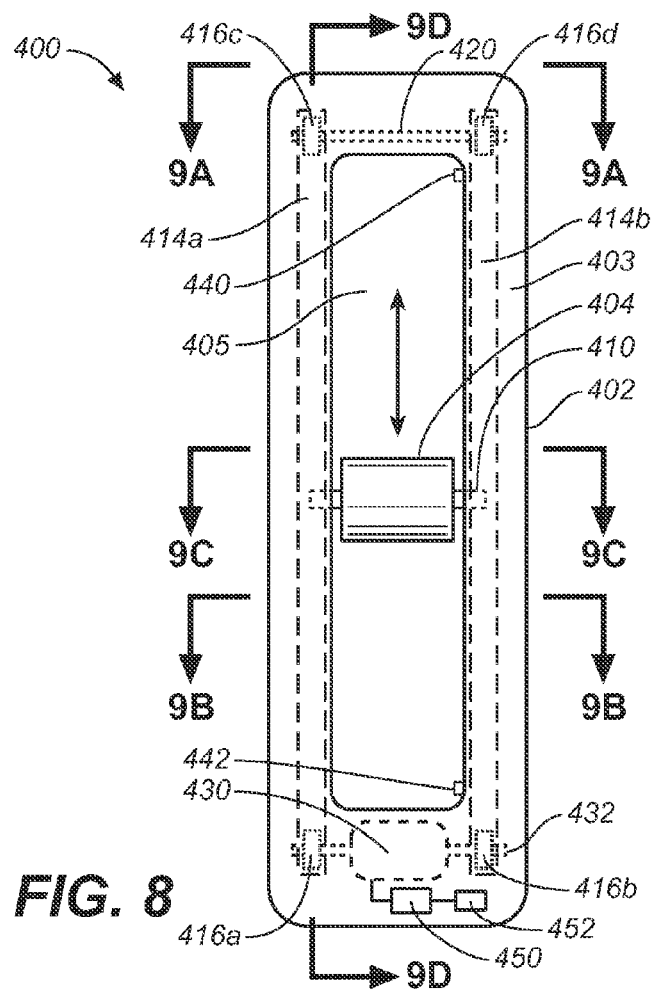
FIG. 8 is a bottom view of the apparatus of FIG. 7.

According to another embodiment of the invention, a compression member is moved along a surface of the patient's limb to apply focused pressure to the target vein. One example of this embodiment is shown in FIGS. 7-9, where exemplary dilation apparatus or device 400 includes a compression member that is driven in one direction and then in a return direction over the target vein. Although various compression member configurations can be used, a roller compression member configuration is shown in the illustrative example. Roller compression member 404 can have a cylindrical shape as shown or any other suitable shape for applying the desired pressure to the patient's limb. For example, compression member 404 can be spherical and form a roller ball that provides more focused pressure than the cylindrical configuration. The spherical roller ball compression member can incorporate the same drive as the cylindrical compression member, which will be described in more detail below, so that it can be moved back and forth along a straight track or path. For example, the spherical roller ball can have an axle that extends through its center like axle 410 described below to accommodate the belt drive illustrated in FIG. 8 or other reciprocating drive mechanism. Further, it should be understood that although a straight track or path is shown, the track or path in any of the embodiments described herein can be configured to form a path corresponding to the path of the target vein if the target vein would otherwise be outside the path of compression member 404.

Returning to FIG. 8, dilation apparatus 400 includes casing 402, which is a rigid casing made from plastic or other suitable material, and which supports compression member 404. Casing 402, which forms a recess in which compression member 404 and the drive reside, can include straps to secure it to the patient's limb and can include straps identical to and arranged like the fastening straps shown in FIG. 4 in connection with dilation apparatus 300. In one embodiment, casing 402 has a width "CW" (FIG. 9A) of 3-6 cm, a height of 2-3 cm, and a length which provides sufficient space for the compression member and which can correspond to the length of casing 302. Referring to the bottom plan view of casing 402, casing 402 has a bottom surface 403 through which is formed a slot 405 that provides access to interior chamber 406 of casing 402. In the illustrative embodiment, compression member 404 is coupled to housing 402 to travel back and forth along slot 405.

Any conventional drive system can be used to repeatedly move the roller member in a forward and return direction. A belt driven roller drive is shown in the illustrative example of FIGS. 8 and 9A-D. Referring to FIG. 8, roller member 404 has an axle 410 having end portions rotatably mounted in brackets 412a,b, which have openings adapted to receive the end portions of axle 410 and are secured to continuous belts 414a,b. Belts 414a,b can be mounted on cylindrical members or hubs 416a,b,c,d. Members 416a,b are secured to the end portions of axle 432 of motor 430, which is secured to casing 402. Members 416e,d are secured to axle 420, which is rotatably mounted to casing 402. Alternatively, axle 420 can be fixedly secured to casing 402 and members 416c,d rotatably mounted on axle 420. As diagrammatically indicated with the arrow in FIG. 9D, when motor 430, which is secured in casing 402, rotates in one direction, it rotates the belts in that direction and moves compression member 404 along slot 405. And when motor 430 rotates in the opposite direction, it rotates the belts in the opposite direction and moves compression member 404 in the opposite direction along slot 405. Any other suitable arrangement for support belts 414a,b can be used as well. For example, hubs 416a-d can be eliminated and the belts directly coupled to motor axle 432 and axle 420.

Figure 9A:
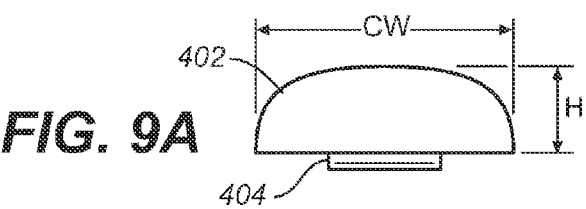
FIG. 9A is an end view of the apparatus of FIG. 8 taken along line 9A-9A.
Figure 9B:
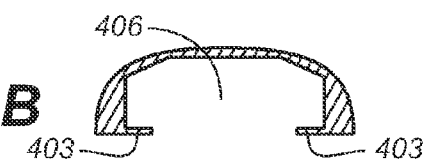
FIG. 9B is a sectional view of the apparatus of FIG. 8 taken along line 9B-9B.
Figure 9C:
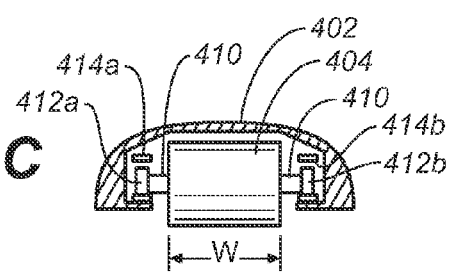
FIG. 9C is a sectional view of the apparatus of FIG. 8 taken along line 9C-9C.
Figure 9D:
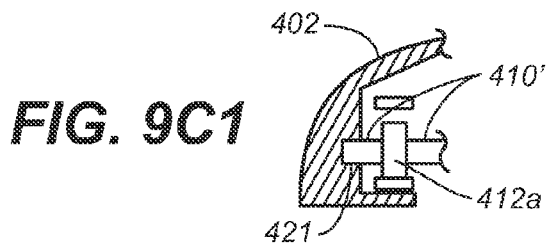
FIG. 9D is a longitudinal sectional view of the apparatus of FIG. 8.
Figure 9D:
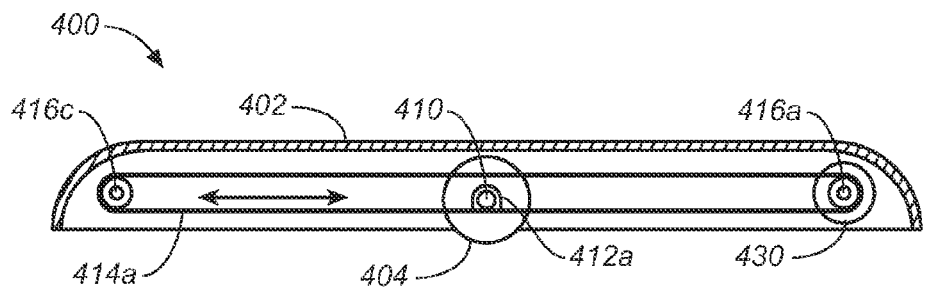

In the variation shown in FIG. 9C1, roller axle 410 is replaced with extended roller axle 410' with each end portion of axle 410' extending into a channel, which is formed in housing 402 and extends the length of slot 403, to limit vertical movement of the roller. Each channel forms a track for compression member 404, which allows the compression member to move along the entire treatment length of the apparatus and, thus, the track or compression member path can have a length equal to the treatment length of the apparatus, which will be described in more detail below. In FIG. 9D, one channel is designated with reference numeral 421. A similar channel (not shown) is provided on the other side of the slot to receive the other end portion of axle 410'. The axle and channel surfaces can be formed of any suitable material to minimize friction therebetween and can be coated or covered with any suitable material as well.

A description of one conventional control is described hereafter for purposes of example. Drive motor 430 may be a DC motor that is coupled to a rechargeable battery 452 via controller or control unit 450. The direction of rotation of the motor and, thus, the direction of movement of the roller along the slot 405, may be controlled by the control unit 450 which controls the polarity of the voltage applied to the motor. Control unit 450 may be coupled to position sensors 440 and 442 (one at each the end of slot 405) to reverse the motor direction when the roller reaches a position sensor. Position sensors 440 and 442 typically are spaced apart a distance that allows the compression member to move along the entire treatment length of the apparatus and, thus, that spacing can be equal to the treatment length. The position sensors can be magnetic or optical sensors or mechanical limit switches. For example, position sensors 440 and 442 can be limit switches, which are engaged by the roller member when the roller member reaches an end of the track (the track being the portion of slot 405 bounded by the position sensors), and which cause the control unit to reverse the polarity of the battery voltage to the motor.

When the motor axle 432 turns in one direction it drives belts 414a,b, which drive the rotatably mounted roller member in one direction. When the roller member reaches the end of the track, it activates a switch, which causes control unit 450 to reverse the motor direction. This causes the roller member to return or move in the opposite direction along the path. When the roller member reaches the other switch, the same sequence occurs and the motor reverses direction and moves the belt and roller member in the other direction. In this manner, intermittent pressure is applied to a plurality of sections of the vein or an infinite number of points on the vein as the roller member moves along its path. Apparatus 400 typically is secured to the patient's limb in a manner in which compression member 404 provides sufficient pressure to the limb to occlude a portion or point of the target vein that is beneath the compression member.

The following describes an exemplary general procedure for creating a fistula in a patient who has end stage renal disease (ESRD) and has elected hemodialysis as a treatment option and then describes an illustrative example of vein dilation using any of the vein dilation apparatus described above to prepare the vein downstream from the fistula for hemodialysis, which example is provided solely for purposes of example and not to limit the invention.

After a patient has elected hemodialysis as the treatment option, the patient's arm veins are evaluated clinically and measured with ultrasound to find out if there is a vein 3 mm or larger. A 3 mm vein is a suitable candidate for surgical connection to an artery.

The patient is brought to the operating room where the surgeon palpates the patient's arm arteries for a pulse to find a target artery to which the selected vein is to be connected. The surgeon then creates a connection between the selected artery and target vein, thereby forming a fistula. In the treatment example illustrated in FIG. 10, the patient's left radial artery was connected to the patient's left cephalic vein in the region of the patient's wrist. The cephalic and basilic veins, which are the only major veins in a human's arm and which are the only suitable veins in a human's arm for hemodialysis, are shown in dashed line and designated with reference characters "CV" and "By." The lower portion of the cephalic vein is in the forearm and the upper portion of the cephalic vein is in the upper arm above the elbow.

After the surgery has been completed and the fistula created, dressing is provided over the wound and apparatus constructed according to the principles of the invention (e.g., apparatus 100 (or modified 100 with a multi-cell compression member as shown in FIG. 3), 300, 400, or 400' (described below)) is secured to the patient's limb before the patient leaves the operating room. The apparatus is placed on a patient's forearm (if the fistula were formed at the patient's wrist) or upper arm (if the fistula were formed at the elbow). In either case, the apparatus is arranged so that the compression member is placed downstream from the fistula and over the target vein (vein of interest) to focus pressure provided thereby toward the target vein. The only other veins which will be affected by the treatment are accessory branches coming off the main vein and these are not used for dialysis. In other words, the compression member is placed over the vein proximal to the connection between the target vein and artery, which is referred to as the fistula. The compression member, however, should be arranged so as not to cover the fistula or suture used to close the wound created to provide access to the vein and artery to make the fistula.

Figure 10:
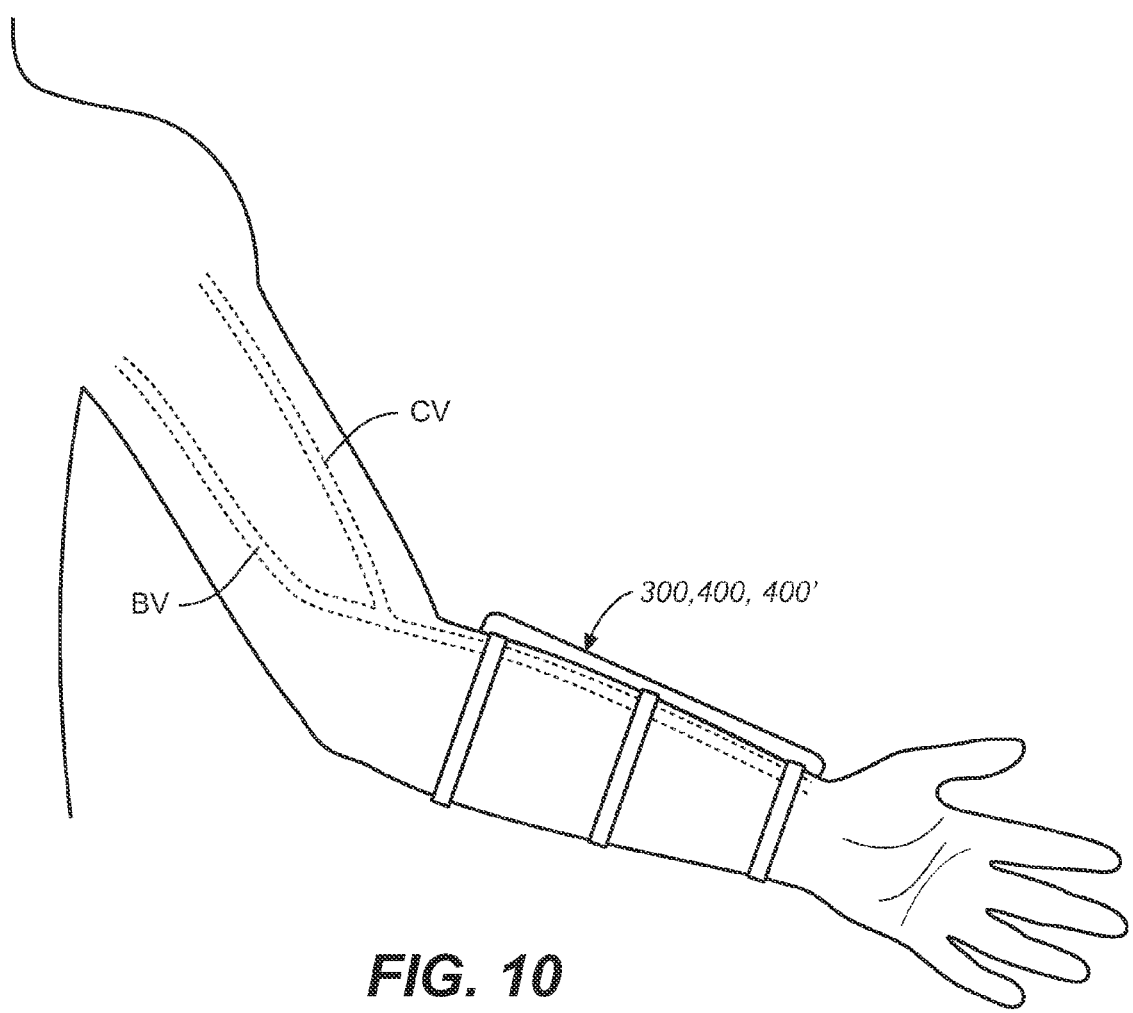
FIG. 10 illustrates use of vein dilation apparatus described herein to dilate a vein in the forearm of a patient.

In the illustrative example, the fistula was created at the patient's left wrist and the apparatus secured to the patient's forearm in a manner to allow intermittent pressure to be applied to the target vein (cephalic vein "CV"), which is to be accessed for hemodialysis, in a manner in which the pressure can be focused on the target vein, with the compression member. As shown in this example, the compression member is configured and arranged to either extend or move in a substantially straight direction along an axial direction or length of the patient's limb without encircling the patient's limb and to exert pressure on a narrow, substantially straight external surface portion of the patient's limb so as to dilate the target vein (e.g., the cephalic vein) thereunder. The compression member extends or runs substantially parallel to the cephalic vein as shown in FIG. 10. As described above, the compression member typically will have a width from 1 cm to and including 2 cm and more typically a width of 1.5 cm.

The compression member applies occlusive pressure on the patient's limb, which is then transmitted to the target vein to temporarily occlude the target vein. In the case where apparatus 100 is used, a substantially uniform pressure is applied intermittently to the target vein. For example, compression member 104 is inflated to a pressure, which is sufficient to occlude the target vein, for about five seconds and then allowed to deflate for about three seconds and this cycle repeated for the treatment period. When the multi-cell apparatus of FIG. 3 or FIG. 4 or roller apparatus 400 is used, the pressure profile can correspond to a wave. In one method, apparatus 300 is configured to pressurize each cell independently so that a pressure wave moves, for example, from the wrist toward the elbow. In one example where the three cell embodiment shown in FIG. 3 is used, the cell closest to the wrist is inflated to a pressure, which is sufficient to occlude the target vein, for about five seconds and allowed to deflate while the middle cell adjacent thereto is inflated to a pressure, which is sufficient to occlude the target vein, for the same period of time, and then the next cell adjacent to the elbow is inflated to a pressure, which is sufficient to occlude the target vein, for the same period of time while the middle cell is allowed to deflate. This cycle is repeated for the treatment period, which corresponds to the period of time in which the apparatus operates continuously on the patient's limb. In a method using apparatus 400, the apparatus is set to move the compression member back and forth over the target vein at a speed of about one cm/sec for the treatment period. The rolling compression member provides a stroking pressure wave to the vein as it moves over it. In this manner, intermittent occlusive pressure is applied to a plurality of sections of or an infinite number of points on the target vein.

The overall treatment and the frequency of the treatment periods used to provide the desired vessel dilation can vary from patient to patient. Treatment periods typically will range from about one to about eight hours and typically will be provided daily up to about eight weeks. The vein dilation can be periodically checked to determine if treatment be continued. The device configuration including its low and narrow profile and its ability to cover the target vein make it especially suitable for relatively long periods of use, while allowing the patient to be relatively active.

The dilation method can include application of heat to the patient's limb with the apparatus as described above. Typically, the heating element(s) will maintain the temperature of the portion of the apparatus in contact with the patient's skin to about 98 to 150° F. In one example, the control unit is set to provide a constant temperature of 120° F. at the surface of the apparatus that contacts the patient's limb.

In a further method, a topical vasodilating agent such as nitric oxide is applied to the patient's skin over the target vein prior to each use of the vein dilation apparatus.

Pressure alone, pressure in combination with heat or the topical dilation agent, or pressure, heat and the topical agent can be used throughout the treatment period.

According to another embodiment of the invention, dilation apparatus constructed according to the principles of the invention is used between hemodialysis sessions, which typically are scheduled three times per week. The apparatus would be worn and pressure applied for up to about an eight hour period during the days when hemodialysis is not scheduled. Such ongoing vein stimulation can help insure vein dilation continues for a longer period of time and provide longer patency of the fistula.

According to another method of the invention, dilation apparatus constructed according to the principles of the present invention is used before the fistula is made. In this method, the apparatus typically will be used daily for about one month before the surgery to dilate the target vein to a desired diameter for the fistula. The pressure and daily treatment periods will be as described above regarding post surgery treatment. The foregoing treatment is carried out to prepare and dilate the vein prior to surgical connection. However, this treatment also can be done to assist in vein dilation proximal to an area where an arterio-venous graft has been constructed to provide dialysis. In this example, the apparatus typically will be applied to the upper arm cephalic vein and the process performed before graft failure.

According to another method of the invention, dilation apparatus constructed according to the principles of the present invention, is applied at a new site to dilate another vein while hemodialysis using the previously dilated vein continues. For example, apparatus being used between hemodialysis sessions can be moved from the left arm cephalic vein to the right arm cephalic vein when the physician concludes that the left arm cephalic vein is nearing failure. Indications of such failure can include, but are not limited to, significantly reduced blood flow from the fistula. In this manner, the patient can commence dilating another vein in preparation for surgical creation of another fistula. This can improve the efficiency of the overall hemodialysis treatment.

Figure 11A:
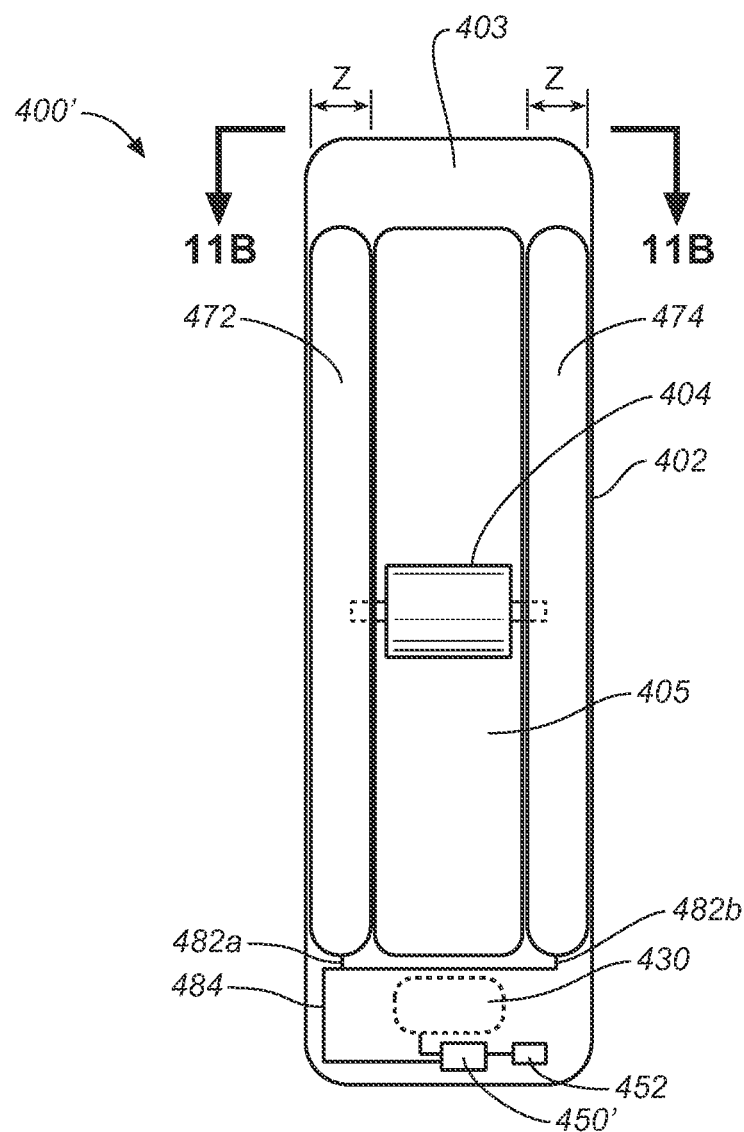
FIG. 11A a bottom view of a variation of the embodiment of FIGS. 7 and 8.
Figure 11B:
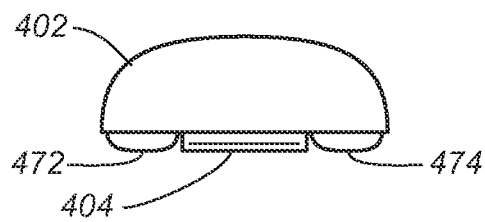
FIG. 11B is an end view of the apparatus of FIG. 11A taken along line 11B-11B.

Referring to FIGS. 11A and 11B, another embodiment of the invention is shown and generally designated with reference numeral 400'. Dilation apparatus or device 400' is the same as apparatus 400 with the exception that apparatus 400' further includes inflatable or expandable compression members or balloons 472 and 474 (which are secured to the bottom surface 403 of housing 402 and extend in a longitudinal direction of housing 402 on opposite sides of slot 405) and their accompanying fluid delivery conduits, and the control unit of apparatus 400 modified to include a pressure source and timing circuit to maintain balloons 472 and 474 inflated throughout the treatment period to partially occlude the branch vessels, which branch from the target vein, while roller compression member 404 moves back and forth over the target vein to transmit a stroking pressure wave thereto to dilate the target vein as described above. In this manner, dilation of the branch vessels, which branch from the target vein, is reduced or minimized during treatment. Balloons 472 and 474 also prevent the branch vessels from carrying blood away from the target vein or they reduce the amount of blood flow that they carry away from the target vein, thus assisting with enlargement of the target vein. The control unit is designated with reference numeral 450' and is coupled to power source 452 in the same manner as control unit 450 is coupled to power source 452 in apparatus 400. Conduits 482a,b are fluidly coupled to manifold 484, which is fluidly coupled to the pressure source in control unit 450', which controls pressure delivery from the pressure source to compression members or balloons 472 and 474. Balloons 472 and 474 may be inflated to provide continuous occlusive pressure to the branch vessel during a treatment period. However, it should be understood that balloons 472 and 474 need not be continuously inflated during a treatment period. Solenoid valves or any suitable means as described above can be used to inflate and/or deflate balloons 472 and 474 according to a desired inflation-deflation profile. The length of balloons or compression members 472 and 474 typically is the same as the length of the track in which or path along which roller compression member 404 moves (i.e., the distance which the roller compression member travels in each direction) and typically will be at least 5 cm as described in more detail below. Further, expandable members or balloons similar to balloons 472 and 474 can be combined with any other embodiment described herein and positioned in a similar manner.

During hemodialysis, two needles typically are used. One needle is used to draw blood, while the other provides a return for filtered blood. The needles typically are spaced apart at least 5 cm and therefore at least 5 cm of dilated vessel may be required. The devices described herein have a treatment length, which corresponds to the length of the expandable member 104 or 104', the distance between the outermost margins of cells 304a and 304d, or the length of the path or track in which the moving (e.g., reciprocating) compression device moves and typically will be at least 5 cm, and more typically the treatment length will be 5-25 cm depending on the size of the patient's limb (e.g., the patient's upper arm or lower arm), and even more typically it will be 20-25 cm. The length of the apparatus housings or casings (e.g., housing or casing 302 or 402), typically will be about 2 cm longer than the apparatus treatment length. The housing or casing length typically will be less than or equal to 40 cm so as not to overlap a patient's joint (e.g., the elbow joint), and more typically will be less than or equal to 30 cm. This apparatus or any of dilation apparatus 100 or modified apparatus 100 with a multi-cell compression member as shown in FIG. 3 and described above, 300, and 400 are constructed to provide long term vein dilation sufficient for hemodialysis or maintenance of vein dilation during hemodialysis treatment.

Any feature described in any one embodiment described herein can be combined with any other feature or features of any of the other embodiments whether preferred or not.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto.

What is claimed is:

1. Vessel dilation apparatus which is a portable ambulant apparatus allowing the patient to be ambulatory when it is secured to the patient for dilating a target vein of a patient comprising:
   a support adapted to be secured to a limb of a patient, said support has a plurality of securing members configured to secure the support to the patient's limb;
   a compression member that is coupled to said support and comprises an inflatable member, said compression member configured to extend in a substantially straight direction along at least a portion of the length of said limb without encircling the limb when said support is secured to the patient's limb, said compression member is configured so that when said support is secured to the patient, the compression member can be positioned to focus pressure toward said target vein;
   a pressure source coupled to said compression member;
   a control unit coupled to said pressure source to control delivery of pressurized fluid to the inflatable member;
   a power source coupled to said control unit; and
   a conduit and one or more fluid control devices, said conduit coupling said pressure source and inflatable member and said one or more fluid control devices being operatively coupled to the control unit and inflatable member.

2. The apparatus of claim 1, wherein said compression member is an inflatable member with a single inflatable cell.

3. The apparatus of claim 2, further including a rigid casing that surrounds a portion of said compression member and forms at least a portion of said support.

4. The apparatus of claim 1, wherein said compression member has a width of 1-2 cm.

5. The apparatus of claim 4, wherein said compression member has a length of at least 5 cm.

6. The apparatus of claim 1, further including a rigid casing that surrounds a portion of said compression member and forms at least a portion of said support.

7. Vessel dilation apparatus for dilating a target vein of a patient comprising:
   a support adapted to be secured to a limb of a patient, wherein said support includes a flexible sheet that can be placed around the limb to form a sleeve, wherein said sheet includes securing members arranged to secure portions of said sleeve together to secure the support to the patient's limb, and wherein said sheet has an inner portion to which said inflatable member is coupled,
   a compression member that is coupled to said support and comprises an inflatable member, said compression member configured to extend in a substantially straight direction along at least a portion of the length of said limb without encircling the limb when said support is secured to the patient's limb, said compression member is configured so that when said support is secured to the patient, a pressure source coupled to said compression member;

a control unit coupled to said pressure source to control delivery of pressurized fluid to the inflatable member, and a conduit and one or more fluid control devices, said conduit coupling said pressure source and inflatable member and said one or more fluid control devices being operatively coupled to the control unit and inflatable member.

8. The apparatus of claim 7, wherein said compression member has a width of 1-2 cm.

9. The apparatus of claim 7, wherein said compression member is configured such that it can be secured to the patient's limb over a target vein that is to be accessed for hemodialysis in a manner in which it can be pressurized to focus intermittent pressure toward said vein over time to dilate said vein.

10. The apparatus of claim 7, wherein said compression member is configured such that it can be secured to the patient's limb to extend substantially parallel to the target vein.

11. Vessel dilation apparatus for dilating a target vein of a patient comprising:

a support adapted to be secured to a limb of a patient;

a compression member that is coupled to said support and comprises an inflatable member, said compression member configured to extend in a substantially straight direction along at least a portion of the length of said limb without encircling the limb when said support is secured to the patient's limb;

fluid control apparatus operatively associated with said inflatable member;

a pressure source coupled to said fluid control apparatus; and a control unit coupled to said pressure source and said fluid control apparatus and configured to control a plurality of cycles of inflating and deflating the inflatable member to provide a plurality of pressure cycles to the target vein, wherein said control unit is configured to control inflation and deflation of the inflatable member according to a predetermined sequence, and wherein said control unit includes a timing circuit and controls inflation and deflation sequence based on the timing circuit.

12. The apparatus of claim 11, wherein the apparatus is a portable ambulant apparatus allowing the patient to be ambulatory when it is secured to the patient.

13. The apparatus of claim 11, wherein said compression member is configured so that when said support is secured to the patient, the compression member can be positioned to focus pressure toward said target vein.

14. The apparatus of claim 11, wherein said support has a plurality of securing members configured to secure the support to the patient's limb.

15. The apparatus of claim 11, wherein said compression member is an inflatable member with a single inflatable cell.

16. The apparatus of claim 11, further including a rigid casing that surrounds a portion of said compression member and forms at least a portion of said support.

17. The apparatus of claim 11, further including a power source coupled to said control unit.

18. The apparatus of claim 11, wherein said support comprises a flexible sheet that can be placed around the limb to form a sleeve.

19. The apparatus of claim 18, wherein said sheet includes securing members arranged to secure portions of said sleeve together to secure the support to the patient's limb.

20. The apparatus of claim 19, wherein said sheet has an inner portion to which said inflatable member is coupled.

21. The apparatus of claim 19, wherein said compression member has a width of 1-2 cm.

22. The apparatus of claim 11, wherein said support comprises a plurality of securing members arranged to secure the support to the patient's limb.

23. The apparatus of claim 22, wherein said compression member has a width of 1-2 cm.

24. The apparatus of claim 11, wherein said fluid control apparatus comprises a solenoid valve.

25. The apparatus of claim 11, further including a rigid casing that surrounds a portion of said compression member and forms at least a portion of said support.

26. The apparatus of claim 11, wherein said compression member is configured such that it can be secured to the patient's limb over a target vein that is to be accessed for hemodialysis in a manner in which it can be pressurized to focus intermittent pressure toward said vein over time to dilate said vein.

27. The apparatus of claim 11, wherein said compression member is configured such that it can be secured to the patient's limb to extend substantially parallel to the target vein.

28. Vessel dilation apparatus for dilating a target vein of a patient comprising:

a support adapted to be secured to a limb of a patient;

a compression member that is coupled to said support and comprises an inflatable member, said compression member configured to extend in a substantially straight direction along at least a portion of the length of said limb without encircling the limb when said support is secured to the patient's limb;

fluid control apparatus operatively associated with said inflatable member;

a pressure source coupled to said fluid control apparatus; and a control unit coupled to said pressure source and said fluid control apparatus and configured to control a plurality of cycles of inflating and deflating the inflatable member to provide a plurality of pressure cycles to the target vein, wherein said compression member comprises a plurality of inflatable cells, said fluid control apparatus is operatively coupled to said plurality of inflatable cells, and said control unit, which is coupled to said control apparatus, is configured to control a plurality of cycles of inflation and deflation of said inflatable cells.

29. The apparatus of claim 28, wherein said control unit controls inflation and deflation of said cells for a preset period of time.

30. The apparatus of claim 28, wherein said fluid control apparatus comprises a plurality of solenoid valves.

31. The apparatus of claim 28, wherein said support comprises a plurality of securing members arranged to secure the support to the patient's limb.

32. The apparatus of claim 31, wherein the apparatus is a portable ambulant apparatus allowing the patient to be ambulatory when it is secured to the patient.

33. The apparatus of claim 31, wherein said compression member has a width of 1-2 cm.

34. The apparatus of claim 33, wherein said compression member has a length of at least 5 cm.

35. Vessel dilation apparatus for dilating a target vein of a patient comprising:

a support adapted to be secured to a limb of a patient;

a compression member that is coupled to said support and comprises an inflatable member, said compression member configured to extend in a substantially straight direction along at least a portion of the length of said limb without encircling the limb when said support is secured to the patient's limb;

said compression member having a length and comprising a plurality of inflatable cells that are serially arranged along said length and are sequentially inflatable.

36. The apparatus of claim 35, wherein the inflatable cells are separate, longitudinally spaced cells along said length.

37. The apparatus of claim 35, wherein the apparatus is a portable ambulant apparatus allowing the patient to be ambulatory when it is secured to the patient.

38. The apparatus of claim 37, wherein said compression member is configured so that when the apparatus is secured to the patient, the compression member can be placed over said target vein to focus pressure toward said target vein.

39. The apparatus of claim 38, wherein the compression member has a width of 1-2 cm.

40. The apparatus of claim 38, wherein said support has a plurality of securing members configured to secure the support to the patient's limb.

41. The apparatus of claim 40, further including a rigid casing that surrounds a portion or said compression member and forms at least a portion of said support.

42. The apparatus of claim 38, wherein said compression member is configured such that it can be secured to the patient's limb over a target vein that is to be accessed for hemodialysis in a manner in which it can be pressurized to focus intermittent pressure toward said vein over time to dilate said vein.

43. The apparatus of claim 38, wherein said compression member is configured such that it can be secured to the patient's limb to extend substantially parallel to the target vein.

44. Vessel dilation apparatus for dilating a target vein of a patient comprising:
a support adapted to be secured to a limb of the patient, wherein the support includes securing members configured to secure said support to a patient's limb;
a compression member being movably coupled to said support to move along a substantially straight path extending along at least a portion of the length of said limb and exert pressure on a substantially straight external surface of the patient's limb without encircling the limb when said support is secured to said limb;
said compression member being positionable so that when the compression member is moved along said surface it applies focused pressure toward the target vein, and
a drive system for moving said compression member in a forward and return direction.

45. The apparatus of claim 44, wherein said compression member has a width of 1-2 cm.

46. The apparatus of claim 44, wherein the compression member is rotatably coupled to said support.

47. The apparatus of claim 44, further including first and second expandable members, each extending adjacent to said substantially straight path, which extends between said first and second expandable members.

48. The apparatus of claim 44, wherein the apparatus is a portable ambulant apparatus allowing the patient to be ambulatory when it is secured to the patient.

49. The apparatus of claim 44, wherein said compression member is configured such that it can be secured to the patient's limb over a target vein that is to be accessed for hemodialysis in a manner in which it can be pressurized to focus intermittent pressure toward said vein over time to dilate said vein.

50. The apparatus of claim 44, wherein said compression member is configured such that it can be secured to the patient's limb to run substantially parallel to the target vein.

* * * * *